United States Patent
Weill et al.

(10) Patent No.: US 9,138,544 B2
(45) Date of Patent: Sep. 22, 2015

(54) METHOD OF MANUFACTURING A DISPOSABLE EJECTION DEVICE

(75) Inventors: David Weill, Begnins (CH); Pierre-Yves Chassot, Thoiry (FR)

(73) Assignee: Primequal S.A., Begnins (CH)

( * ) Notice: Subject to any disclaimer, the term of this patent is extended or adjusted under 35 U.S.C. 154(b) by 194 days.

(21) Appl. No.: 12/937,354

(22) PCT Filed: Apr. 8, 2009

(86) PCT No.: PCT/IB2009/051475
§ 371 (c)(1),
(2), (4) Date: Oct. 11, 2010

(87) PCT Pub. No.: WO2009/125353
PCT Pub. Date: Oct. 15, 2009

(65) Prior Publication Data
US 2011/0030191 A1    Feb. 10, 2011

(30) Foreign Application Priority Data

Apr. 10, 2008 (FR) ...................................... 08 01972

(51) Int. Cl.
*A61M 5/31* (2006.01)
*A61M 5/315* (2006.01)
(Continued)

(52) U.S. Cl.
CPC ......... *A61M 5/31581* (2013.01); *A61M 5/1782* (2013.01); *A61M 5/3148* (2013.01); *A61M 5/31526* (2013.01); *A61C 5/062* (2013.01); *A61M 5/24* (2013.01); *A61M 5/3129* (2013.01);
(Continued)

(58) Field of Classification Search
CPC . A61M 2005/341; A61M 5/502; A61M 5/24; A61M 2005/2492; A61M 5/1782; A61M 5/31581; A61M 2005/2407; A61M 5/31595; A61M 5/3129; B23P 19/00; B23P 11/00
USPC ............... 29/890.09, 428, 777, 423; 604/209, 604/218, 224, 229
See application file for complete search history.

(56) References Cited

U.S. PATENT DOCUMENTS 3,967,759 A * 7/1976 Baldwin et al. ................ 222/129
4,150,464 A * 4/1979 Tracy .............................. 24/313
(Continued)

FOREIGN PATENT DOCUMENTS

CN    1655837 A    8/2005
EP    0 080 793 A    6/1983
(Continued)

OTHER PUBLICATIONS

Office Action dated Oct. 9, 2012 issued in the corresponding Chinese patent application No. 200980111652.X citing the following document : FR2535206A1.
(Continued)

*Primary Examiner* — David Bryant
*Assistant Examiner* — Ruth G Hidalgo-Hernande
(74) *Attorney, Agent, or Firm* — Frommer Lawrence & Haug LLP

(57) ABSTRACT

Method of manufacturing a device for ejecting a liquid or pasty product, characterized in that it comprises the following steps: drawing a product (11) to be ejected within a volume (10) of a container holder (2*a*) of the ejection device by means of a pull rod (18); removing the pull rod (18) from the container holder (2*a*); assembling a rear body (2*b*) on the container holder (2*a*) in order to form the ejection device.

16 Claims, 7 Drawing Sheets

(51) Int. Cl.
*A61M 5/178* (2006.01)
*A61C 5/06* (2006.01)
*A61M 5/24* (2006.01)
*A61M 5/50* (2006.01)
*A61M 5/34* (2006.01)

(52) U.S. Cl.
CPC ............ *A61M 5/31595* (2013.01); *A61M 5/502* (2013.01); *A61M 2005/2407* (2013.01); *A61M 2005/2492* (2013.01); *A61M 2005/341* (2013.01); *Y10T 29/49826* (2015.01); *Y10T 29/53* (2015.01)

(56) References Cited

U.S. PATENT DOCUMENTS

| | | | |
|---|---|---|---|
| 4,444,560 A * | 4/1984 | Jacklich | 604/224 |
| 4,581,022 A * | 4/1986 | Leonard et al. | 604/229 |
| 5,413,563 A * | 5/1995 | Basile et al. | 604/218 |
| 5,433,352 A * | 7/1995 | Ronvig | 222/391 |
| 6,096,002 A * | 8/2000 | Landau | 604/68 |
| 7,448,868 B2 * | 11/2008 | Delval et al. | 433/89 |
| 2001/0049506 A1 | 12/2001 | Schoenfeld et al. | |
| 2002/0173752 A1 | 11/2002 | Polzin | |
| 2003/0105430 A1 | 6/2003 | Lavi et al. | |
| 2005/0119612 A1 | 6/2005 | Delval et al. | |
| 2006/0178642 A1* | 8/2006 | Gillespie et al. | 604/228 |
| 2006/0264838 A1 | 11/2006 | Volckmann et al. | |

FOREIGN PATENT DOCUMENTS

| | | |
|---|---|---|
| EP | 1 263 387 B | 9/2004 |
| FR | 2535206 A | 5/1984 |
| JP | 58-86175 A | 5/1983 |
| JP | 2007-098698 A | 4/2007 |
| WO | WO 01/60311 A | 8/2001 |
| WO | WO 03/082387 A | 10/2003 |
| WO | WO 2005/007224 A | 1/2005 |

OTHER PUBLICATIONS

Office Action dated Nov. 25, 2012 issued in the corresponding Cuban patent application No. 2010-0197 citing the following document : FR2535206A1.

Office Action dated Mar. 27, 2013 issued in the corresponding Cuban patent application No. 2010-0197 citing the following document : FR2535206A1.

Office Action dated Apr. 18, 2013 issued in the corresponding Vietnamese patent application No. 1-2010-03005.

Office Action dated Oct. 15, 2012 issued in the corresponding Ukraine patent application No. a 2010 12136 citing the following documents : FR2535206A1 and US2003105430A1.

Office action issued by Japanese Patent Office for corresponding Japanese application 2011-503535 mailing date Apr. 16, 2013 with English translation.

Office action issued by Chinese Patent Office for corresponding Chinese application 200980111652.X, dated Sep. 5, 2013 with English translation.

\* cited by examiner

METHOD OF MANUFACTURING A DISPOSABLE EJECTION DEVICE

This application is a 371 of PCT/IB2009/051475 filed on Apr. 8, 2009, published on Oct. 15, 2009 under publication number WO 2009/125353 A which claims priority benefits from French Patent Application Number 08/01972 filed Apr. 10, 2008, the entire disclosure of which is incorporated herein by reference.

The invention concerns a method of fabricating a device for ejecting a liquid or paste product. It also concerns a kit for fabrication of such a device.

There is known from patent application FR 2 535 206 a dental syringe for intra-ligamentary injection. This syringe enables the injection of a product via a very fine and flexible needle into the ligaments situated between the jaw bone and the tooth. It consists mainly of an elongate body on which is mounted a mechanism commanding injection by the displacement of a thrust cylinder, a container-holder in which is accommodated a container filled with liquid to be injected, and an end-piece including the injection needle. To solve problems of difficult access to the areas in which the injections must be made, the body of the syringe has an injection head at an angle to the axis of the body of the syringe. The removable needle is placed on the body before carrying out the injection and then removed afterwards. The mechanism commanding the injection primarily comprises a lever articulated to the syringe body and operating on a thrust cylinder via a pawl articulated to the lever and urged toward a position of contact with the teeth of a rack produced on the thrust cylinder. The cylinder is guided in translation in a bore produced in the syringe body. It also has a longitudinal groove cooperating with a screw that is screwed radially relative to the bore and projects into it to prevent rotation of the cylinder. The mechanism also includes a non-return pawl preventing rearward movement of the thrust cylinder when actuation of the lever ceases. This non-return pawl is urged into a position of contact with the teeth of the rack and may be moved away from that position by action on a button to cancel the injection pressure and/or to change the container of product to be injected on which the thrust cylinder bears. Such a device has drawbacks. On the one hand, its production is complex and costly. On the other hand, it has numerous parts and complex shapes, in particular, angles and corners in the material. These angles and corners form highly inaccessible areas and consequently are very difficult to clean and thus difficult to sterilize.

To alleviate the above problems, the document WO2005/007224 proposes an easily demountable and cleanable ejection device of simpler construction. This device comprises a body, a part intended to contain the product and provided with an orifice for ejecting the product, a thrust cylinder provided with teeth moving in a bore in the body and varying the volume of the part intended to contain the product, and a mechanism for displacing the thrust cylinder linked to the body, comprising a demountable articulated lever, acted on by a return spring, operating on the teeth of the thrust cylinder via a pawl articulated to the lever and urged into a position of contact with the thrust cylinder by a spring and a non-return pawl urged toward a position of contact with the thrust cylinder. Despite its greater simplicity and the presence of a demountable lever facilitating cleaning, this device still does not achieve a satisfactory degree of hygiene and still necessitates difficult cleaning. Moreover, the demountable connection of the lever with the body of the device is obtained to the detriment of the efficacy of the device, because it weakens the lever, on which high forces are exerted during ejection. Finally, like the previous one, this solution necessitates at least partial pre-assembly before its distribution, as otherwise its assembly would be too laborious because of the number of parts in the device.

Finally, all existing solutions rely on complex devices the fabrication process of which is costly. Moreover, they are unsatisfactory in terms of hygiene.

Thus a general object is to propose a method of fabricating a device for ejecting a liquid or paste product alleviating the drawbacks of existing solutions.

To be more precise, a first object of the invention is to propose an economical method of fabricating an ejection device.

A second object of the invention is to propose a method of fabricating a device for ejecting a liquid or paste product offering a maximum degree of hygiene.

To this end, the invention provides a method of fabricating a device for ejecting a liquid or paste product comprising the following steps:

aspiration of a product to be ejected into a volume of a container-holder of the ejection device using a puller member;

demounting the puller member from the container-holder;

assembling a rear body to the container-holder to form the ejection device.

The method may comprise a preliminary step of assembling the puller member directly or indirectly with a piston of the container-holder of the ejection device closing the volume to be filled. To this end, the connection between the puller member and the piston of the container-holder may be effected by screwing the end of the puller member into the piston.

The fabrication method may moreover comprise a preliminary step of fixing a tool to the front end of the container-holder. To this end the anterior end of the container-holder may have a shape globally inclined relative to the body but having a surface having at least one generatrix substantially parallel to the axis of this body in order to enable straight insertion of a needle type tool in this direction before bending it and fixing it in an inclined working position.

The fabrication method may instead comprise a preliminary step of assembling with the container-holder a syringe type device having an elongate cylindrical body delimited in its rear part by a piston mobile in longitudinal translation and comprising in its front part a needle retained by an end-piece.

The method may moreover comprise an intermediate step of assembling a lever onto the rear body. To this end the lever may comprise a forwardly extending horizontal upper part intended to be manipulated and a lower end in the form of an axle that is positioned in a corresponding location of the rear body.

The fabrication method may instead comprise an intermediate step of assembling a rack with the rear body by inserting it through an opening.

The step of assembling the rear body and the container-holder may be effected by clipping at least two lateral blades of a first element extending longitudinally and having an outwardly oriented protuberance intended to cooperate with corresponding openings on the second element. To this end the step of assembling the rear body and the container-holder may be irreversible.

The method may additionally comprise the assembly of a rack into the device, this rack being adapted to move in a certain direction to cause ejection of the product and movement of which in the opposite direction is impossible to prevent refilling of the device.

The method of fabricating an ejector device may comprise at least three steps of injection molding plastic material to form three separate parts of the device: a lever integrating a pawl, a container-holder and a rear body.

The fabrication method may further comprise a fourth step of injection molding plastic material to form a rack.

The assembly of the rear body onto the container-holder may comprise a connection between ejection means of the rear body and a piston of the container-holder so that the product may be ejected from the container-holder by action on these ejection means of the rear body.

The invention also relates to a kit, i.e. a set of elements, for fabricating a device for ejecting a liquid or paste product comprising a container-holder, a rear body and a puller member.

To this end the puller member may be separate from the container-holder and have a connecting member for its direct or indirect connection to a piston of the container-holder.

The fabrication kit may further comprise a lever comprising a pawl and a rack intended for a connection with the rear body.

The fabrication kit may further comprise a tool-holder and a needle type tool both adapted to be connected to the container-holder.

These and other objects, characteristics and advantages of the present invention are disclosed in detail in the following description of one particular embodiment of the present invention given by way of nonlimiting example with reference to the appended figures in which.

In the preferred embodiment of the invention, the method of fabricating the injection device relies on assembling four separate main elements of simple shape enabling their fabrication in plastic material by simple injection molding.

Figure 1:
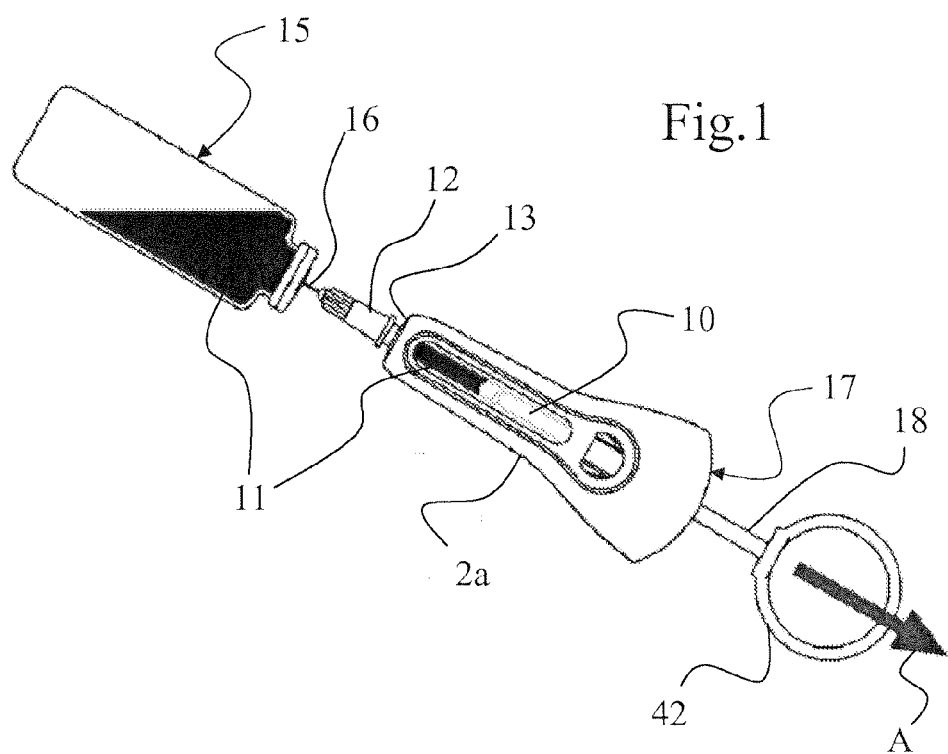
FIGS. 1 to 3 represent diagrammatically assembly steps of a method of one embodiment of the invention of fabrication of an ejection device.
Figure 2:
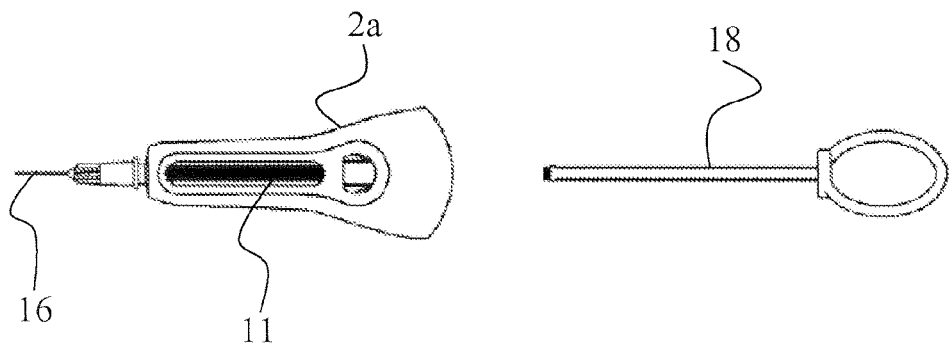
Figure 3:
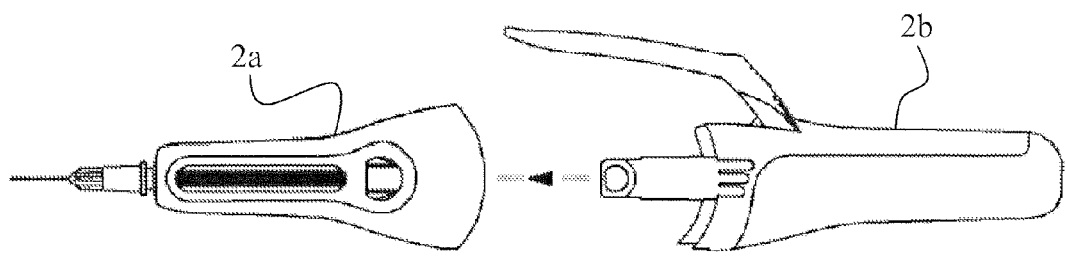

The method of fabricating this ejection device comprises the following essential steps, illustrated by FIGS. 1 to 3.

In a first step illustrated by FIG. 1, the volume 10 of the container-holder 2a of the ejection device is filled with the product 11 to be ejected by aspirating it from a storage flask 15. To this end, the container-holder 2a is equipped at its front end 13 with a tool-holder 12 for fixing a needle 16. Toward its rear end, the container-holder 2a comprises an opening 17 through which a puller member 18 in the form of a rod mobile in the longitudinal direction along the length of the container-holder 2a has been inserted and connected to the piston 19 delimiting the volume 10 carrying the content to be ejected. By pulling on the puller member 18, the user pulls the piston 19, which is in an advanced position at the beginning of this step, toward the rear, in the direction A, which leads to aspiration of the product 11 from the flask 15 into the volume 10 of the container-holder 2a. Note that the puller member 18 is provided with a holding ring 42 in its rear part to facilitate its manipulation.

In a second step illustrated by FIG. 2, which is undertaken when the container-holder 2a contains the required quantity of product 11, the puller member 18 is detached from the piston 19. This puller member is a component that is not part of the ejection device but is used only in this intermediate phase to enable simple and advantageous filling of the ejection device.

Figure 4:
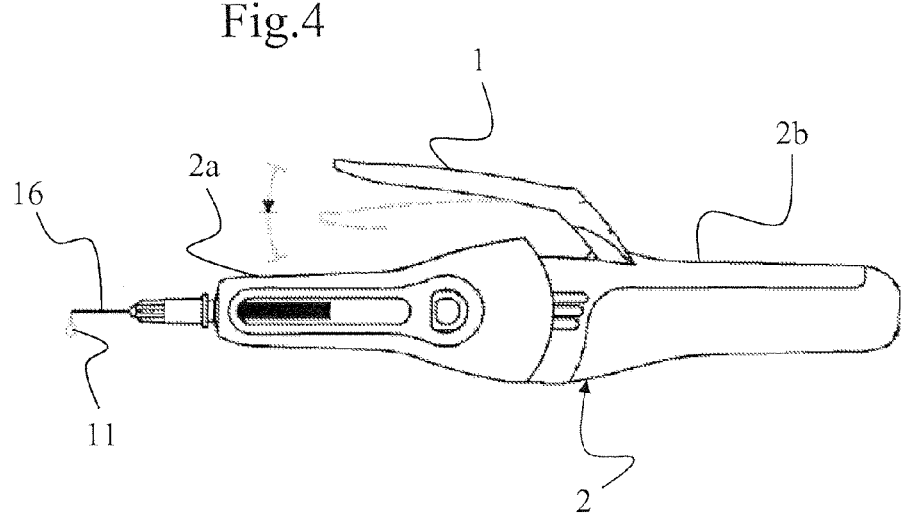
FIG. 4 represents the ejection device obtained by the fabrication method of this embodiment of the invention.

In a third step illustrated by FIG. 3, the ejection device is definitively assembled by mounting a rear body 2b on the container-holder 2a, the rear body having the mechanical function of ejecting the product 11 contained in the container-holder 2a. To this end, it comprises ejection means that act on the piston 19 of the container-holder 2a as described in detail hereinafter. At the end of this third step, as illustrated by FIG. 4, the ejection device is ready for use. The assembled two parts 2a and 2b form a single body 2. Actuation of the lever 1 ejects the product 11 from the container-holder 2a via the end of the needle 16.

Figure 5A:
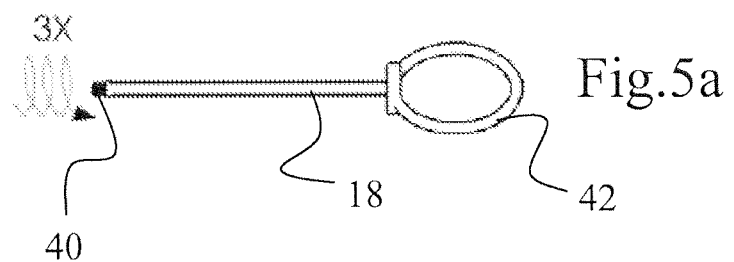
FIGS. 5a and 5b represent a detail of these assembly steps of one embodiment of the invention.
Figure 5B:
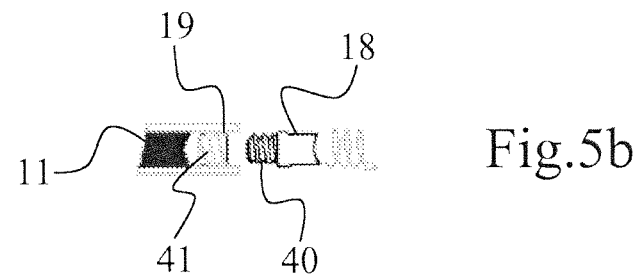

FIGS. 5a and 5b show the connection between the puller member 18 and the piston 19 of the container-holder 2a, which is a screwed connection, the front end of the puller member comprising a threaded part 40 cooperating with a threaded part 41 provided in the piston 19. In this embodiment, simply screwing in or out by three turns respectively connects and separates the puller member and the piston. Any other variant direct or indirect connection between these two elements is nevertheless possible. Thus the first step described hereinabove with reference to FIG. 1 is preceded by a step of mounting the puller member 18 on the piston 19, in a step that is the opposite of the step 2 of the method of demounting the puller member.

Figure 6:
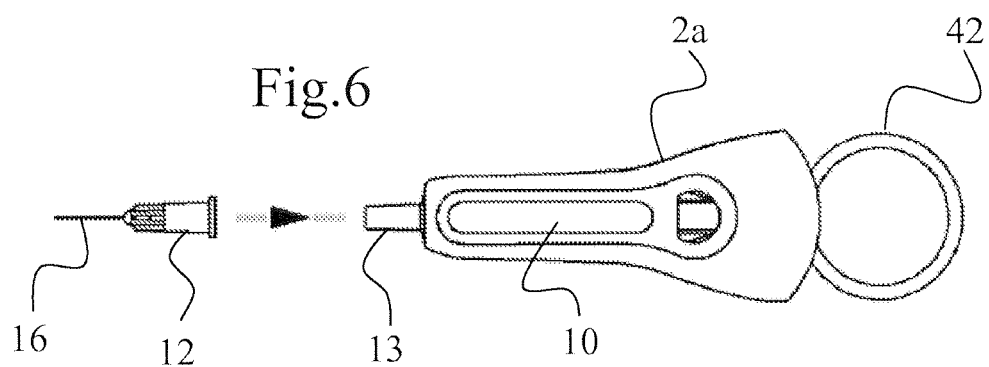
FIG. 6 illustrates a preliminary step of the fabrication method of one embodiment of the invention.

FIG. 6 illustrates a preliminary step of one embodiment of the invention that consists in fixing a needle 16 to the front end 13 of the container-holder by means of a tool-holder 12, here a needle-holder. This fixing may be effected by screwing or any other quick connection method. In an advantageous variant, this connection may be effected in accordance with the teaching of the document WO03/082387. To this end, the anterior shape 13 of the container-holder 2a is a shape that is inclined overall relative to the body 2 but has a surface having at least one generatrix substantially parallel to the axis of the body 2a in order to enable straight-line insertion of the needle 16 in this direction before flexing it and fixing it in the inclined working position, as illustrated by the FIG. 11 variant.

Figure 7A:
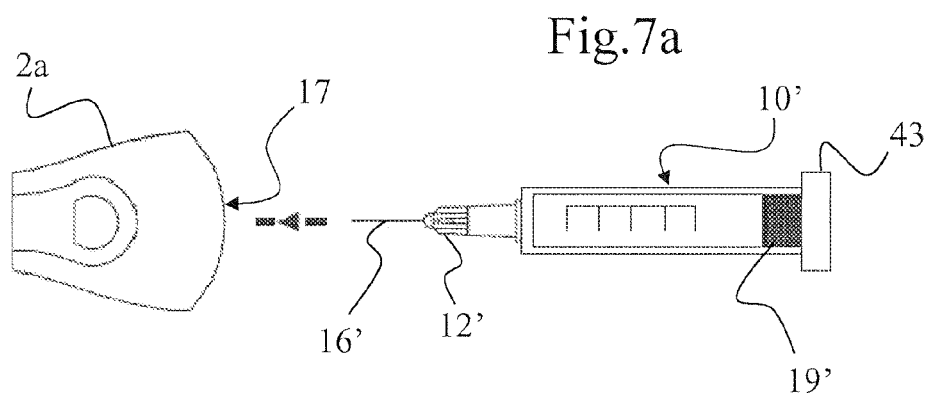
FIGS. 7a and 7b illustrate a variant execution of the aforementioned preliminary step in one embodiment of the invention.
Figure 7B:
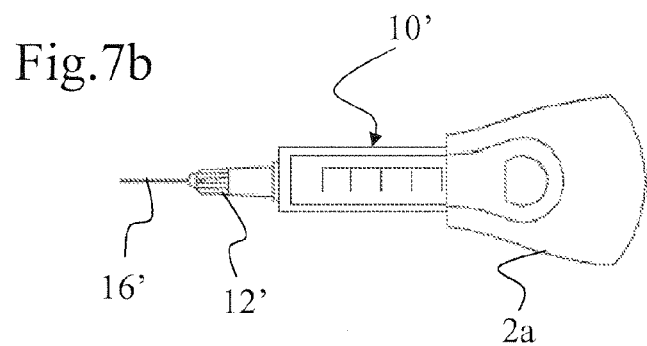

FIGS. 7a and 7b illustrate a variant of the above preliminary step, which consists in integrating a syringe type device 10' comprising a needle 16' retained by an end-piece 12' on an elongate cylindrical body delimited in its rear part by a piston 19' mobile in longitudinal translation. This syringe 10' is inserted into the container-holder 2a through its rear opening 17 until its rear base 43, which forms a shoulder, comes into abutting engagement in its final position. This variant also makes it possible to obtain a container-holder assembly similar to the configuration illustrated by FIG. 1. Thus the volume 10' of the container-holder and the piston 19' may be independent components assembled to the container-holder or elements that are part of the structure of the container-holder.

The above variant thus illustrates that the end 13 of the container-holder and the end-piece 12 for fixing the tool may be one and the same. Such a configuration is advantageous in the context of a device for ejecting glue, for example.

Figure 8:
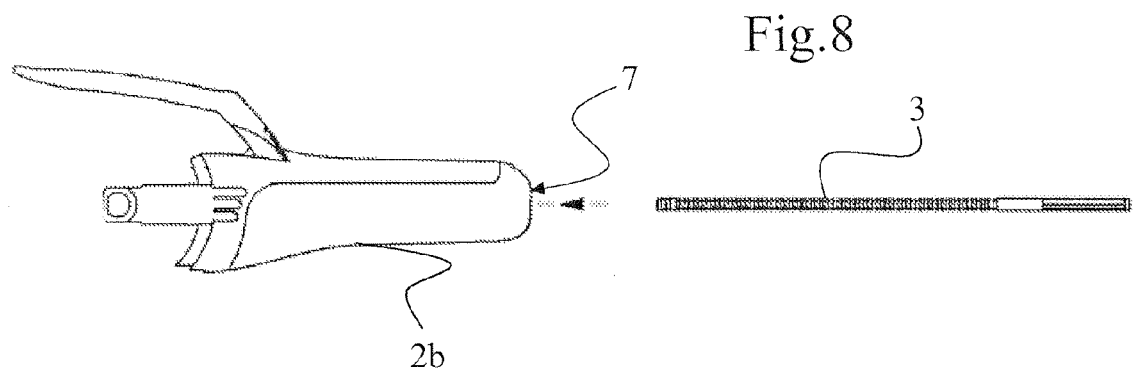
FIG. 8 illustrates an intermediate step of one embodiment of the invention.

FIG. 8 shows an intermediate step of the assembly process, preceding the final step 3, which consists in assembling a rack 3 with the rear body 2b by inserting it through a rear opening 7 in the rear body until it reaches a position in which its front face cooperates with the piston 19 of the container-holder.

Figure 9:
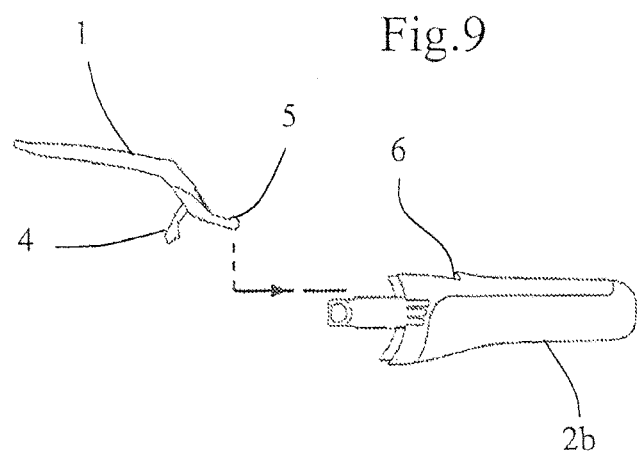
FIG. 9 represents a perspective view of an intermediate assembly of the lever of the ejection device.
Figure 10:
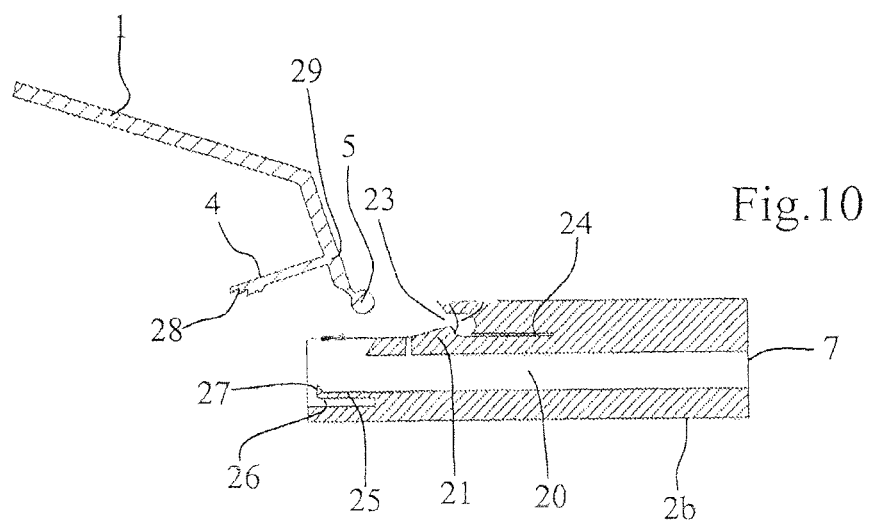
FIG. 10 represents a view in section of the intermediate assembly of the lever of the ejection device.

FIGS. 9 and 10 illustrate another intermediate step of the assembly method, preceding the final step 3, which consists in assembling a lever 1 to the rear body 2b. The lever 1 comprises a horizontal forwardly extending upper part intended to be manipulated and a lower end in the form of an axle 5 that is positioned in a corresponding location 6 on the rear body 2b. A pawl 4 in one piece with the lever 1 extends downward and toward the interior of the body 2b.

FIG. 10 represents more particularly the connection between the lever 1 and the rear body 2b and shows in detail the elements used during this intermediate phase. The lever 1 comprises a cylindrical end part forming the axle 5 on which it rotates, which is housed in a cylindrical location 6 of corresponding diameter formed in the upper part of the rear body 2b of the device. This cylindrical location 6 comprises in its lower portion a longitudinal leaf spring 21 integrated into the body 2b formed by a cut-out 24 in a part of the upper surface of the central cylindrical bore 20 of the rear body 2b. The axle 5 is first positioned on two lateral rails, not shown, in the upper part of the body 2 and then displaced toward the rear by sliding on these rails toward the opening 23 of the final location 6, the dimension of which opening is smaller than the diameter of the axle 5, the spring 21 retracting downward in the bore 20 under the pressure of the axle 5 of the lever 1 to allow it to pass and reach its location 6 via this opening 23. The spring 21 then resumes its natural position thanks to its elasticity and comes to espouse a lower part of the circumference of the axle 5.

The lever 1 is also connected to a pawl 4 substantially perpendicular to the lever in a connecting area 29. This pawl 4 terminates at an end 28 comprising one or more teeth to cooperate with the rack 3, which is not yet connected to the body 2b. The pawl and the rest of the lever 1 form a one-piece structure obtained by a single injection molding step. Their connecting area 29 is such that the pawl 4 is mobile elastically relative to the lever 1 in rotation about its connection 29 with the lever. To this end, cut-outs or thinner areas are provided in the plastic material in the connecting area 29 to form an area of lower stiffness deformable relative to the rest of the lever. These cut-outs may for example define an axle extending over the width of the lever in the area 29 and connected to the pawl 4 to act as its rotation axis.

Finally, the rear body 2b has at least one non-return pawl 25 in the form of a longitudinal leaf spring provided by a cut-out 26 in the body itself, and thus formed during the injection molding of the body 2b, and having a pointed end 27 complementary in shape to the teeth of the rack 3 extending in the bore 20 to cooperate with these teeth as described in detail hereinafter.

When the lever is in position in the location 6 of the body 2b, a rack 3 is inserted into the longitudinal cylindrical bore 20 of the body assembled in this way through a rear opening 7, as illustrated by FIG. 8. This insertion of the rack 3 into the bore 20 of the body 2 causes it to come to bear on the lower surface of the leaf spring 21 for insertion of the lever 1, thereafter preventing any downward movement of the leaf spring 21. In this way, the axle 5 of the lever 1 is locked into the location 6 of the body 2, and is no longer able to escape via the smaller opening 23.

Figure 11:
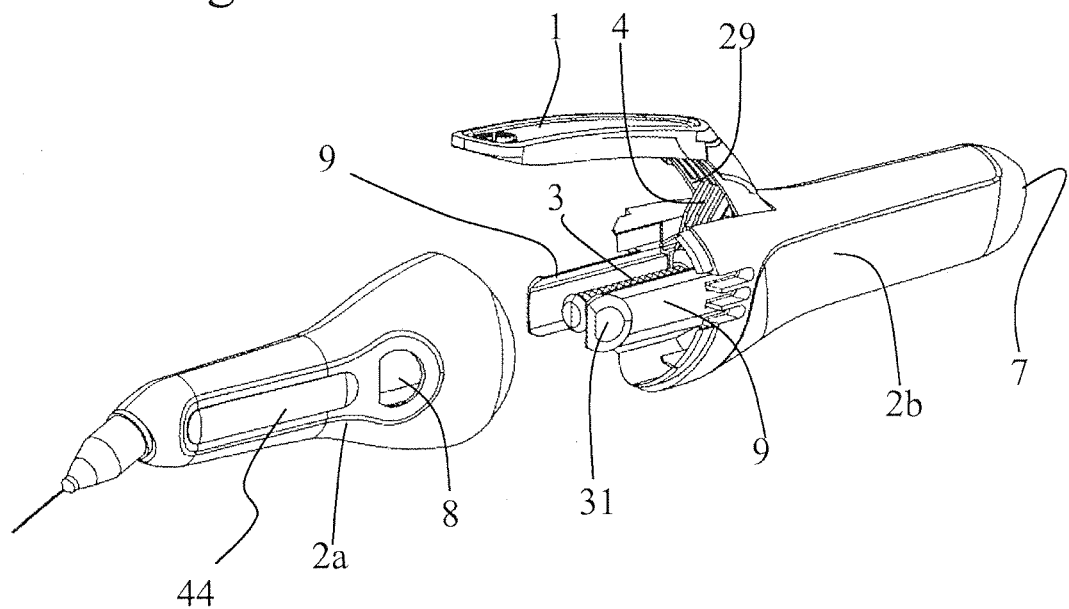
FIG. 11 represents a perspective view of the final assembly step of the ejection device of one embodiment of the invention.
Figure 12:
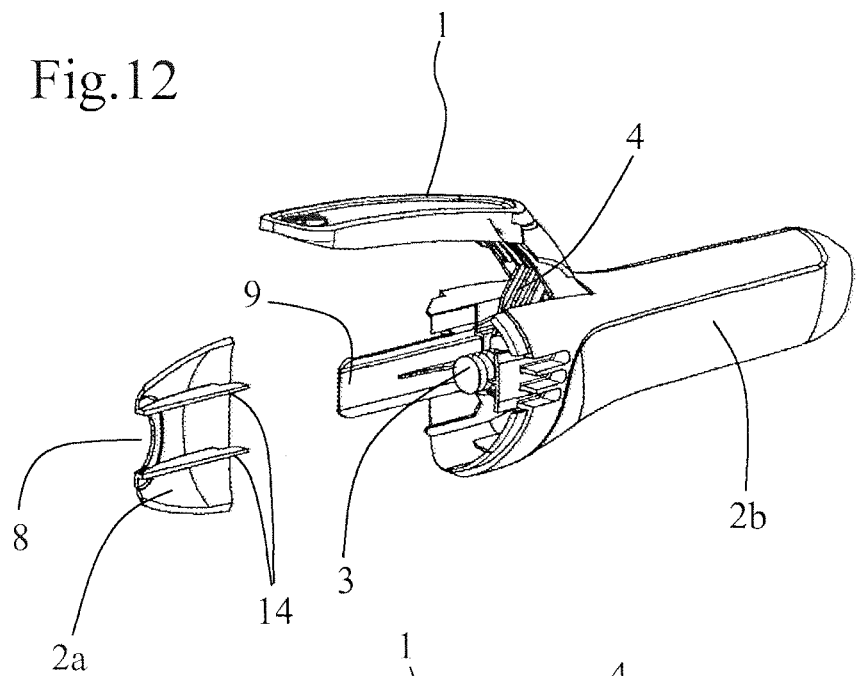
FIGS. 12 and 13 represent partial perspective views of the latter step in order to illustrate complementary elements.
Figure 13:
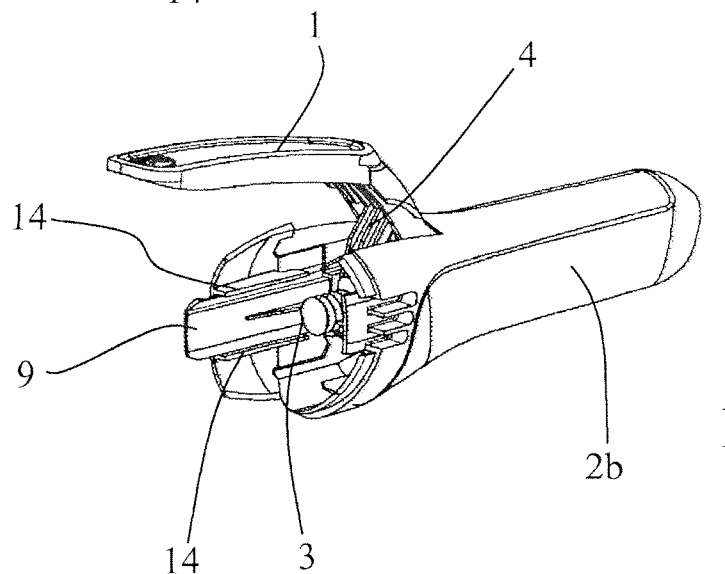

FIGS. 11 to 13 illustrate more precisely the step 3 of final assembly of the rear body 2b comprising the ejection mechanics on the container-holder 2a in the preferred embodiment of the invention. To produce this assembly, the rear body 2b has two lateral blades extending longitudinally forward and adapted to cooperate with complementary lower and upper rails 14 on the interior lateral walls of the container-holder 2a. The end of these blades 9 has an outwardly-oriented protuberance 31 adapted to cooperate with corresponding openings 8 of the container-holder 2a. On insertion of the blades 9 into the rails 14 of the container-holder 2a, the protuberances 31 rub against the interior lateral walls of the container-holder 2a, causing elastic deformation of the blades 9 toward the interior of the body 2. As soon as the protruberances 31 reach the corresponding shape openings 8 they enter therein because of the spring effect of the blades 9, which return to their initial normal spacing and their longitudinal and parallel direction, in accordance with a clipping principle. The elongate shape of the blades 9 retained over their length by their lower and upper rails 14 makes possible a rigid, sturdy and without play connection between the two parts 2a and 2b of the body to withstand effectively the forces exerted on them in use. Any other equivalent mechanical connection between these two parts might be suitable. Alternatively, the blades 9 could in particular be on the container-holder 2a and the corresponding openings 8 in the rear body. Moreover, this connection could be of a hook/tab type obtained by rotation of the two parts, by clipping, by a single blade or hook, etc.

In an advantageous embodiment of the device, the volume 10 of the container-holder 2a extends as far as the blades 9 at the level of the openings 8 so that reverse movement of the rear body 2b, which would necessitate further deformation of the blades 9 by pressing on the protruberances 31 to extract them from the openings 8 at the same time as pulling the body 2b toward the rear, is made difficult or even impossible. This geometry thus prevents the protuberances 31 escaping in this way and makes possible locking or quasi-locking of the body 2 assembled in this way, which is therefore not demountable or only demountable with great difficulty, i.e. the assembly is irreversible or quasi-irreversible.

Figure 14:
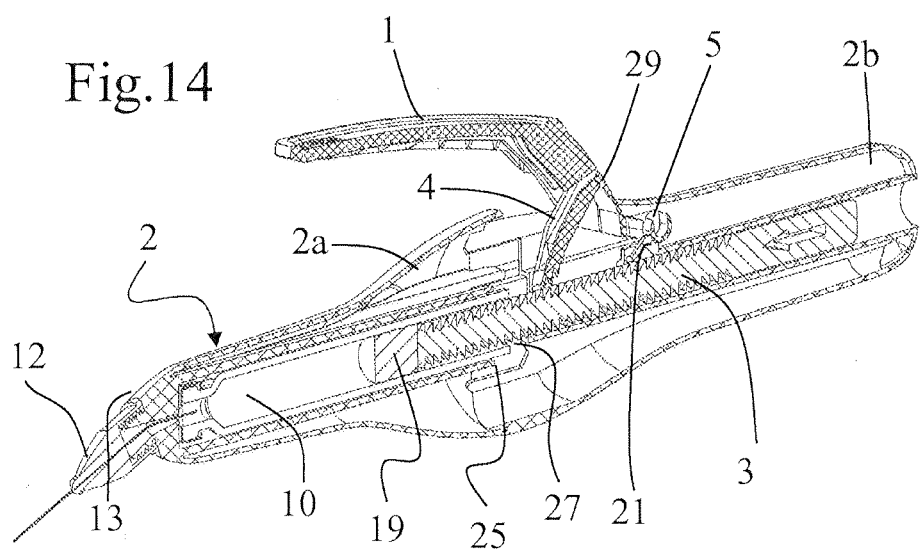
FIG. 14 represents a view of the ejection device of this embodiment of the invention in front perspective sectioned on a longitudinal vertical plane passing approximately through the middle of the device.

FIG. 14 illustrates in section the assembled device of a variant embodiment. The toothed end 28 of the pawl 4 of the ejection device, seen particularly clearly in FIG. 10, penetrates into an upper opening of the body 2 to enter an area close to the teeth of the rack 3 and the end part 27 of the non-return pawl comes to be housed in a tooth of the rack. The insertion of the rack 3 in the bore 20 is accompanied by an audible click when the end 27 of the non-return pawl 25 takes up its position between two teeth of the rack. As this end 27 of the non-return pawl 25 occupies a position slightly more advanced than that of the end 28 of the pawl 4, this audible click occurs when the rack is sufficiently advanced to be operated by the lever 1, and this click serves to inform the user that the rack has been advanced sufficiently.

The lever 1 is pressed downward against the container-holder 2a by a rotation about the axle 5, leading to elastic deformation of the pawl 4 bearing on the rack 3 about its area 29 of connection to the lever, thanks to the flexibility of the material used and the chosen geometry at the level of the connection 29 between the pawl 4 and the lever 1 in particular. This movement of the pawl 4 enables its toothed end 28 that cooperates with the teeth of the rack 3 to apply a thrust force to the rack and advance it within the bore 20 to act on the piston 19 and to cause ejection of the product 11 contained in the device.

When the lever is released, the pawl 4 exerts an elastic return force toward its initial position and draws the lever 1 towards its initial high position. In this phase, the non-return pawl 25 prevents the rack from moving backwards.

This embodiment guarantees the disposable character of the device, which may be used only once to eject the chosen volume of product. This is guaranteed by the combination of two main factors:
  the connection between the two parts 2a, 2b of the body is irreversible or quasi-irreversible;
  when the piston is at the end of its stroke after ejection of the product, it remains locked in this position by the rack, backward movement of which is impossible because of the non-return pawl. It is therefore not possible to refill the volume of the container-holder.

As explained above, a fast and low-cost method of fabricating the ejection device of a preferred embodiment consists in fabricating separately by injection molding the four different essential components of the device in plastic material: the lever 1, the container-holder 2a, the rear body 2b and the rack 3. The material used may be polyamide, polypropylene, ABS or any other plastic material. A plastic material that can be recycled is highly suitable for the device as it is disposable after use. A transparent plastic material may advantageously be used, notably for the container-holder 2a, to make it possible to see the remaining volume of product to be ejected, at least through a window 44. Alternatively, the above components may be fabricated differently and in other materials. The rack 3 may be produced in stainless steel, for example.

The method of fabricating the ejection device thereafter comprises the three essential steps described above for filling and final assembly of the above components.

The fabrication method has been described in the context of an anesthetic syringe type device in the dental field. More generally, the method is adapted to fabricate an ejection device for medical use for injecting products such as anesthetics into hard tissues or for depositing glues, resins or amalgams. It may equally be used in the paramedical field to deposit particular quantities of collagen. It may further be used in the micromechanics and jewelry field to effect gluing or microwelds or to deposit products. Accordingly, the toolholder 12 present at the end 13 of the body of the device may hold tools other than a needle 16.

Finally, the solution achieves the sought objectives and has the following advantages:
  the device is based on a simple structure with few elements, with no separate and independent spring or axle, producible easily and at low cost, by methods compatible with the use of materials that may be recycled: the fabrication method is therefore economical and compatible with a disposable device concept, which thus makes it possible to eliminate the problems of cleaning and to achieve a much higher level of hygiene;
  the method makes possible easy filling of the ejection device, preceding a final phase of assembly that may be irreversible and thus impose the disposable character of the device to achieve a guaranteed hygiene;
  the simple and easy filling step of the method of the invention avoids having to provide a step of filling by an industrial process and thus greatly simplifies the fabrication method;
  the composition of the device in few elements easy to assemble facilitates its distribution and its assembly and final filling at the moment an injection is required; this solution therefore makes it possible to market an intermediate product comprising at least two unassembled parts of the device: a container-holder 2a and a body 2b, together with a puller member; this furthermore enables the end user to choose the product they wish to inject and the required dose;
  the presence of a locked and perfectly fixed lever makes it possible to achieve high-performance ejection.

The device of the present invention has been designed on the basis of the disposable device concept. Nevertheless, its non-disposable use, using the cleaning methods of the prior art, will not depart from the scope of the invention. The simplicity of the fabrication method makes it possible to make it just as easily demountable, for example by modifying the connection between the bodies 2a and 2b to facilitate the escape of the arms 9. In such a solution, cleaning it would be greatly simplified because of the simplification of the structure of the device.

The invention claimed is:

1. A method of fabricating a device for ejecting a liquid or paste product, wherein the method comprises the following steps in order:
  aspiration of a product to be ejected into a volume of a container-holder of the ejection device using a puller member acting on a piston in the container-holder;
  demounting the puller member from the container-holder;
  removal of the puller member from the device for ejecting the liquid or paste product;
  assembling a lever onto a rear body, the rear body having a rear opening and a leaf spring,
  wherein the lever incorporates a forwardly extending horizontal upper part and a lower end in the form of an axle;
  inserting the axle into the rear body along an axis of the rear body, the leaf spring of the rear body deforming to receive the axle;
  assembling the rear body to the container-holder; and
  inserting a rack through the rear opening until the rack causes the leaf spring to lock the axle along the axis and reaches a position in which a front face of the rack acts on the piston enabling ejection of the product from the volume.

2. The method of fabricating a device for ejecting a liquid or paste product as claimed in claim 1, wherein the method comprises a preliminary step of fixing a tool to the front end of the container-holder.

3. The method of fabricating a device for ejecting a liquid or paste product as claimed in claim 1, wherein the method comprises a preliminary step of assembling with the container-holder a syringe type device having an elongate cylindrical body delimited in its rear part by a piston mobile in longitudinal translation and comprising in its front part a needle retained by an end-piece.

4. The method of fabricating a device for ejecting a liquid or paste product as claimed in claim 1, wherein the step of assembling the rear body and the container-holder is effected by clipping at least two lateral blades of a first element extending longitudinally and having an outwardly oriented protuberance intended to cooperate with corresponding openings on the second element.

5. The method of fabricating a device for ejecting a liquid or paste product as claimed in claim 1, wherein the method comprises at least three steps of injection molding plastic material to form three separate parts of the device: the lever integrating a pawl, the container-holder and the rear body.

6. The method of fabricating a device for ejecting a liquid or paste product as claimed in claim 1, wherein the assembly of the rear body onto the container-holder comprises a connection between ejection means of the rear body and the piston of the container-holder so that the product may be ejected from the container-holder by action on these ejection means of the rear body.

7. The method of fabricating a device for ejecting a liquid or paste product as claimed in claim 1, wherein the method comprises a preliminary step of assembling the puller member directly or indirectly with the piston of the container-holder of the ejection device closing the volume to be filled.

8. The method of fabricating a device for ejecting a liquid or paste product as claimed in claim 7, wherein the connection between the puller member and the piston of the container-holder is effected by screwing the end of the puller member into the piston.

9. The method of fabricating a device for ejecting a liquid or paste product as claimed in claim 7, wherein the puller member used to aspirate the product is not part of the injection device, wherein the puller member comprises a threaded part configured to cooperate with a threaded part in the piston comprises.

10. The method of fabricating a device for ejecting a liquid or paste product as claimed in claim 2, wherein the anterior end of the container-holder has a shape globally inclined relative to the body but having a surface having at least one generatrix substantially parallel to the axis of this body in order to enable straight insertion of a needle type tool in this direction before bending it and fixing it in an inclined working position.

11. The method of fabricating a device for ejecting a liquid or paste product as claimed in claim 4, wherein the step of assembling the rear body and the container-holder is quasi-irreversible.

12. The method of fabricating a device for ejecting a liquid or paste product as claimed in claim 11, wherein the rack is adapted to move in a certain direction to cause ejection of the product, and movement of the rack in the opposite direction is prevented to prevent refilling of the device.

13. The method of fabricating a device for ejecting a liquid or paste product as claimed in claim 5, wherein the method comprises a fourth step of injection molding plastic material to form the rack.

14. A kit for fabricating a device for ejecting a liquid or paste product, comprising:
  a container-holder, a rear body having a rear opening and a leaf spring, and a demountable puller member, a rack that moves along the rear opening inside the rear body, and a lever incorporating a pawl for acting on the rack and an axle rotatable about an axis of the rear body, wherein
  the container holder is configured to allow aspiration of a product into a volume of the container-holder using a puller member;
  the demountable puller member is configured to demount from the container-holder after aspiration, wherein the puller member used to aspirate the product is not part of the injection device;
  the lever is configured to be assembled to the rear body with the leaf spring forming a portion of the axis and being deformable to receive the axle, wherein the rack when inserted in the rear opening causes the leaf spring to lock the axle;
  the rear body is configured to be assembled to the container-holder to form an ejection device.

15. The kit as claimed in claim 14 for fabricating a device for ejecting a liquid or paste product, wherein the puller member is separate from the container-holder and has a connecting member for its direct or indirect connection to a piston of the container-holder.

16. The kit for fabricating a device for ejecting a liquid or paste product as claimed in claim 14, wherein the kit further comprises a tool-holder and a needle type tool both adapted to be connected to the container-holder.

* * * * *